US008871727B2

(12) United States Patent
Meyer et al.

(10) Patent No.: US 8,871,727 B2
(45) Date of Patent: Oct. 28, 2014

(54) ECTOPARASITICIDAL METHODS AND FORMULATIONS

(75) Inventors: Jeffery Alan Meyer, Greenfield, IN (US); William Hunter White, Greenfield, IN (US); Joseph Raymond Winkle, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 594 days.

(21) Appl. No.: 12/816,400

(22) Filed: Jun. 16, 2010

(65) Prior Publication Data

US 2010/0324129 A1 Dec. 23, 2010

Related U.S. Application Data

(60) Provisional application No. 61/218,502, filed on Jun. 19, 2009, provisional application No. 61/262,256, filed on Nov. 18, 2009.

(51) Int. Cl.

*A61K 31/7048* (2006.01)
*A01N 25/00* (2006.01)
*A01N 43/22* (2006.01)
*A61K 31/704* (2006.01)

(52) U.S. Cl.

CPC .............. *A01N 43/22* (2013.01); *A61K 31/704* (2013.01)
USPC .............................................. 514/28; 424/405

(58) Field of Classification Search

USPC .............................................. 514/28; 424/405
See application file for complete search history.

(56) References Cited

U.S. PATENT DOCUMENTS

| | | | | |
|---|---|---|---|---|
| 6,001,981 | A | 12/1999 | DeAmicis et al. | |
| 6,664,237 | B1 | 12/2003 | Snyder | |
| 6,800,614 | B2 | 10/2004 | Lewer et al. | |
| 6,927,210 | B1 | 8/2005 | Thompson et al. | |
| 6,933,318 | B1 | 8/2005 | Kassebaum et al. | |
| 7,683,161 | B2 | 3/2010 | Podhorez et al. | |
| 8,178,500 | B2 | 5/2012 | Qin et al. | |
| 2005/0032716 | A1* | 2/2005 | Lowe et al. | 514/28 |
| 2007/0104750 | A1* | 5/2007 | Wilson et al. | 424/405 |
| 2010/0286076 | A1* | 11/2010 | Snyder et al. | 514/28 |

FOREIGN PATENT DOCUMENTS

| | | |
|---|---|---|
| WO | WO 01/11962 | 2/2001 |
| WO | WO 01/12156 | 2/2001 |
| WO | WO 2008096231 | 8/2008 |
| WO | 2009/030238 | 3/2009 |
| WO | WO 2010/023171 A2 | 4/2010 |

OTHER PUBLICATIONS

Gamal A.El Kady, H.M. El Sharabasy, M.F. Mahmoud and I.M. Bahgat, "Toxicity of Two Potential Bio-insecticides Against Moveable Stages of *Tetranychus urticae* Koch", Journal of Applied Sciences Research, 3(11): 1315-1319, 2007.*

Thomas C. Sparks, Gary D. Crouse, James E. Dripps, Peter Anzeveno, Jacek Martynow, Carl V. DeAmicis and James Gifford, "Neural network-based QSAR and insecticide discovery: spinetoram", Journal of Computer Aided Molecular Design, (2008) 22:393-401.*

International Search Report and Written Opinion of PCT/US2010/038768, mailed Sep. 24, 2010.

Huang et al., 'Recent Advances in the Biochemisry of Spinosyn, Appied Microbiology and Biotechnology, pp. 13-23, 82(1) (2009).

'Dow AgroSciences Receives First Global Registron for Spinetoram Insecticide,' Dow AgroSciences Newsroom, Corporate News, Aug. 10, 2007.

Dow AgroSciences Spinetorarn Technical Bulletin, Nov. 2006.

* cited by examiner

*Primary Examiner* — Sue Liu
*Assistant Examiner* — Nathan W Schlientz
(74) *Attorney, Agent, or Firm* — McAndrews Held & Malloy, Ltd.

(57) ABSTRACT

Provided are novel methods and formulations for topically controlling ectoparasite infestations in animals using spinetoram or a pharmaceutically acceptable salt thereof.

14 Claims, No Drawings

ECTOPARASITICIDAL METHODS AND FORMULATIONS

Ectoparasites such as fleas, lice, blowflies, mosquitoes, ticks and mites are problematic for man and animal alike. Such pests seriously impact productivity in the domesticated animal industry by reducing weight gain, causing poor quality hide, wool, and meat, and in some cases resulting in death. Ectoparasites also cause disease and discomfort in companion animals. Ectoparasites are known to carry bacteria and viruses which are pathogenic to humans. The diseases which ectoparasites cause include malaria, lymphatic filariasis, trachoma, trypanosomiasis, and river blindness, for example.

Efforts for controlling ectoparasites have included the use of insecticides and pesticides. For example, spinosyns, which are naturally derived fermentation products, have been employed as ectoparasiticides in animals and humans. (Snyder, U.S. Pat. Nos. 6,063,771 and 6,664,237; Kassebaum et al., U.S. Pat. No. 6,933,318; and Janssen et al., U.S. Pat. No. 7,030,095).

Derivatives of spinosyns have been employed in agricultural applications. (DeAmicis et al., U.S. Pat. No. 6,001,981). Spinetoram is the common name for a mixture of 25-90%, preferably 50-90% (2R,3aR,5aR,5bS,9S,13S,14R,16a-5,16bR)-2-(6-deoxy-3-O-ethyl-2,4-di-O-methyl-1-.alpha.-L-mannopyranosyloxy)-13-[(2R,5S,6R)-5-(dimethylamino) tetrahydro-6-methylpyran-2-yloxy]-9-ethyl-2,3,3a,4,5,5a,5b,6,9,10,11,12,13,14,16a,16b-hexadecahydro-14-methyl-1H-as-indaceno[3,2-d]oxacyclododecine-7,15-dione (referred to as "dihydro-Et-J", formula I below), and 10-75%, preferably 10-50% (2R,3aR,5aS,5bS,9S,13S,14R,16aS,16b5)-2-(6-deoxy-3-O-ethyl-2,4-di-O-methyl-1-.alpha.-L-mannopyranosyloxy)-13-[(2R,5S,6R)-5-(dimethylamino) tetrahydro-6-methylpyran-2-yloxy]-9-ethyl-2,3,3a,5a,5b,6,9,10,11,12,13,14,16a,16b-tet-radecahydro-4,14-dimethyl-1H-as-indaceno[3,2-o]oxacyclododecine-7,15-dione (referred to as "Et-L", formula II below).

Formula I

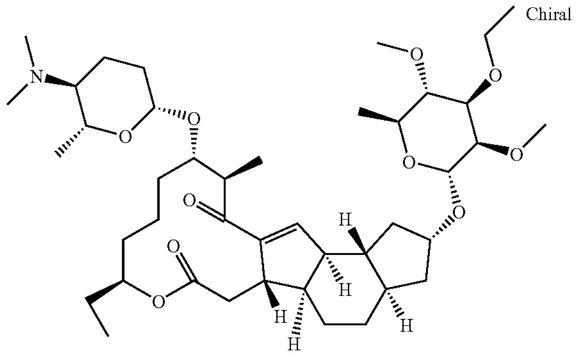

Formula II

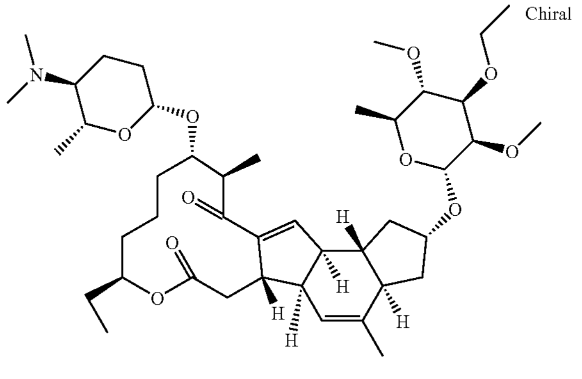

(Podhorez et al., US 2008/0108800A1). Spinetoram is described as providing long-lasting control of a broad spectrum of insect pests in a variety of crops (Dow AgroSciences Spinetoram Technical Bulletin, November 2006). It has been reported spinetoram has been registered in New Zealand as an insecticide in the pome fruit market ("Dow AgroSciences Receives First Global Registration for Spinetoram Insecticide," Dow AgroSciences Newsroom, Corporate News, Aug. 10, 2007).

While the use of spinosyns and other insecticides and pesticides have been beneficial, alternative or improved formulations and methods are needed. Desirable formulations and methods would not only provide alternative therapies, but would also overcome at least some limitations of current therapies. Such limitations include toxicity and safety, efficacy (potency and duration), and resistance issues. Also impacting the beneficial use of insecticides and pesticides are administration obstacles, which include mode and recurrence of administration. For example, reducing the frequency of administration while maintaining efficacy is desirable, as dosing animals is often inconvenient and/or difficult. The present invention encompasses ectoparasiticidal methods and formulations for use in animals which provide alternative options for combating ectoparasiticite infestations. Further, they overcome at least some limitations in the use of current insecticides and pesticides, particularly in providing effective long term, safe, topical control of ectoparasites. The invention provides excellent speed-of-kill and residual efficacies.

The invention provides methods of controlling ectoparasite infestations of an animal by topically administering an effective amount of spinetoram or a pharmaceutically acceptable salt thereof to the animal, as well as pharmaceutical formulations for topically controlling ectoparasite infestations using spinetoram or a pharmaceutically acceptable salt thereof, and a pharmaceutically acceptable carrier. The invention also provides methods for controlling flea infestations of a dog or cat by topically administering an effective amount of spinetoram or a pharmaceutically acceptable salt thereof to said dog or cat. Another aspect of the methods and formulations using spinetoram is the ability to provide prolonged topical control of ectoparasite infestations, thus decreasing the recurrence of dosing an animal, such as no more than every one or two weeks, or every month or more, as well as initial knock-down efficacy.

The host animal may be a mammal or non-mammal, such as a bird (turkeys, chickens) or fish. Where the host animal is a mammal, it may be a human or non-human mammal. Non-human mammals include domestic animals, such as livestock animals and companion animals. Livestock animals include cattle, camellids, pigs, sheep, goats, and horses. Companion animals include dogs, rabbits, cats, and other pets owned and maintained in close association with humans as part of the human-animal bond. For cats, the animal preferably is eight weeks or older.

Ectoparasites include insect and acarine pests which commonly infest or infect animals, and include the egg, larval, pupal, nymphal, and adult stages thereof. Such pests include fleas, lice, mosquitoes, mites, ticks, and blood-sucking, biting or nuisance fly species. A particular target is fleas, and more particularly *Ctenocephalides felis*. *Pediculus humanus* and *Pthirus pubis* are two particular targets in humans.

"Controlling" refers to either ameliorating or eliminating a current infestation, or preventing an infestation, in an animal host.

"Topically" is defined as applying to the outside surface area of an animal or human, and includes the skin or hair. This does not include non-trivial systemic, such as transdermal, application.

"Effective amount" refers to the amount of spinetoram, or a salt thereof, sufficient to control an ectoparasite, and includes causing a measurable reduction in the ectoparasite infestation population. This control may be the result of spinetoram or its conjugate or salt entering the system of the pest when it feeds, or through a repellant action due to the presence of spinetoram or its conjugate or salt thereof. Ranges for spinetoram or a salt thereof in the methods range from greater than 0.01 to 1000, desirably 0.1 to 500, and more desirably 10 to 350, mg/kg of weight of the animal.

"Pharmaceutically acceptable" as used in this application, for example with reference to salts and formulation components such as carriers and ingredients, includes "veterinary acceptable" and "dermatological acceptable", and thus includes both human and animal applications.

Pharmaceutically acceptable salts, and common methodology for preparing them are known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977. Examples of salts include, but are not limited to, salts formed by standard reactions with both organic and inorganic acids such as sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids The term "carrier" is used herein to describe any ingredient other than the active components in a formulation. The choice of carrier will to a large extent depend on factors such as the particular mode of administration, the effect of the carrier on solubility and stability, and the nature of the dosage form.

Spinetoram and its salts may be formulated as pharmaceutical compositions for topical administration. Such pharmaceutical compositions and processes for making the same are known in the art. Spinetoram or its salts may be present in the formulations in amounts greater than 0% to 90%, desirably 0.1% to 50%, and more desirably 1% to 45%, all weight percentages. A particular formulation comprises about 39.6% of spinetoram or a pharmaceutically acceptable salt thereof, on a pure basis, with the remainder of the formulation being one or more carriers. The present formulations can also contain other optional ingredients, such as: antioxidants, buffering agents, preservatives, surfactants, chelating agents, humectants, miscibilizing agents, UV-absorbing compounds or photostabilizers, viscosity-modifying agents, antimicrobial agents, other active agents, dyes, perfumes, conditioners, deodorants and physiologically or dermatological acceptable diluents, excipients or adjuvants. Such agents are known in the art. Such optional ingredients can be, for instance: benzyl alcohol, from 30-65%, and more normally 45-60%, by weight; Dowanol DPM, from 0 to 15%, and more normally 0 to 10% by weight; and other ingredients, such as butylated hydroxytoluene (BHT) from 0 to 2%, and more normally 0.1 to 1.0%, by weight.

Administration of spinetoram or a salt thereof may be topically administered by any suitable application. The compound and formulations can be administered topically to an animal by the direct laying on or spreading of the composition on the skin or hair. Formulations can be applied by spot-on application, plunge or spray dipping, jetting with a hand held spray or in a race, or as a back-line spray or pour-on. The administration can occur daily, weekly, biweekly, or monthly, depending on the severity of the infestation and exposure to the pest, for instance. While monthly administration is normally preferred in most situations, it should be understood sufficient residual efficacy after dosing extends 5, 6, 7, 8, or 9 weeks or more in some instances. As an example, for *C. felis*, residual efficacy of 90% or more can extend more than 9 weeks post dosing.

The formulations useful in the subject invention involve formulations suitable for topical application to skin or hair, and may be made into a wide variety of product types. These include, but are not limited to solutions, aerosols, lotions, creams, gels, sticks, ointments, pastes, cream rinses, shampoos, and body washes.

Spinetoram was evaluated using in vitro and in vivo bioassays to determine topical activity. In many assays, spinosad was used as a comparator or a historical positive control, while other standards (fipronil, permethrin, imidacloprid) were employed. Spinetoram was employed both as technical active, as well as in formulation.

Larval Packet Test (LPT)/Ticks: Test material is formulated in a 2:1 ratio of trichloroethylene:olive oil. Tissue biopsy bags are saturated with 1 ml of formulated material (n=3 per test level), and bags are allowed to dry under a fume hood for at least 2 hours. Approximately 50-100 larval-stage ticks are placed into each bag, and the bag is sealed using a plastic dialysis clip and incubated for 24 h at 27° C. and 95% relative humidity. Bags are then opened, and live/dead ticks are enumerated. Nonlinear regression is used to model dose-mortality relationship and obtain relative potency ($LD_{50}$) data compared to contemporaneous controls (solvent-only or fipronil).

Adult Stable or House Fly Assay (ASF, AhsF). This assay is conducted essentially as described in White, W. H., S. M. Bauer, X. Zhao et al., Comparison of in vitro and in vivo ectoparasiticide activity of an experimental benzimidazole-carbamate with permethrin and amitraz, *J. Med. Entomol.* 42, 207-211 (2005); and White, W. H., C. M. McCoy, J. A. Meyer et al., Knockdown and mortality comparisons among spinosad-, imidacloprid-, and methomyl-containing baits against susceptible *Musca domestica* (Diptera: Muscidae) under laboratory conditions, *J. Econ. Entomol.* 100, 155-163 (2007).

Test material is formulated in DMSO at 10 mM. Doubling dilutions in like solvent are made to yield 10 testing levels. Materials are diluted in either bovine serum (stable flies) or 5% glucose solution (house flies) to obtain desired exposure concentrations from 200-0.39 μM. Approximately 3 ml of diluted test material is placed into a test tube (n=3 per test level) and a dental wick is used to absorb fluid. One dental wick is placed into a small weigh boat inside of a 100 mm Petri dish. Approximately 10 mixed-sex adult flies are anesthetized using carbon dioxide and counted into each dish. Dishes are incubated at 27° C. and 50-70% relative humidity. Flies recover from anesthesia and feed on compound-soaked dental wicks. After 24 h, live/dead flies are enumerated. Nonlinear regression is used to model dose-mortality relationship and obtain relative potency ($LD_{50}$) data compared to contemporaneous controls (solvent-only or permethrin).

Flea Contact Assay (FCA)/Cat Flea: Test material is formulated in acetone at the desired exposure concentration and doubling dilutions performed to obtain a total of 10 testing levels. Approximately 0.05 ml of formulated material is dispensed into the bottom of a test tube containing a small amount of dog hair. Acetone is allowed to evaporate under a fume hood overnight. Approximately 10 mixed-sex adult cat flea are anesthetized using carbon dioxide and dispensed into each tube. Tubes are sealed using a ventilated plastic cap and incubated at 27° C. and 75-80% relative humidity. After 24 h, live/dead fleas are enumerated. Nonlinear regression is used to model dose-mortality relationship and obtain relative potency ($LD_{50}$) data compared to contemporaneous controls (acetone-only or fipronil).

Table 1 below displays the summary of in vitro characterization for spinetoram (technical) versus standards.

TABLE 1

| Parasite | Compound | Potency (24 h $EC_{50}$ μM) | 95% CI of $EC_{50}$ | Spinetoram:Spinosad Potency Ratio |
|---|---|---|---|---|
| House Fly | Spinetoram | 2.178 | 1.732-2.740 | 5.5 |
| | Spinosad | 11.96 | 9.452-15.13 | |
| | Fipronil | 0.9698 | 0.727-1.293 | |

| Parasite | Compound | Potency ($EC_{50}$ ng/$cm^2$) 24 h | 48 h | 95% CI of $EC_{50}$ 24 h | 48 h | Spinetoram:Spinosad Potency Ratio 24 h | 48 h |
|---|---|---|---|---|---|---|---|
| Cat Flea | Spinetoram | 1.292 | 0.6238 | 0.4817-3.463 | 0.07643-5.091 | 2.4 | 2.4 |
| | Spinosad | 3.084 | 1.500 | 1.806-5.266 | 0.8859-2.540 | | |
| | Permethrin | 63.30 | 0.1580 | 3.306-121.2 | 0.0840-0.2971 | | |
| | Fipronil | 43.56 | 22.18 | 37.20-51.01 | 18.62-26.41 | | |
| | Imidacloprid | 11.59 | 7.737 | 6.083-22.08 | 6.753-8.866 | | |

| Parasite | Compound | Potency ($EC_{50}$) | 95% CI of $EC_{50}$ | Spinetoram/Spinosad Potency Ratio |
|---|---|---|---|---|
| Lone Star Tick | Spinetoram | 531.6 ppm | 411.5-686.6 | 0.4 |
| | Spinosad | 189.6 ppm | 180.3-199.3 | |

Compared with spinosad, spinetoram exhibits significantly greater insecticidal activity in vitro against adult house flies and adult cat fleas (5.5 and 2.4 times more potent, respectively).

Knockdown and Residual Efficacy Testing and Comparison of Spinetoram with Elector® for Controlling House Flies on Treated Panels.

Test material concentrates of spinetoram (120 g/L suspension concentrate) and spinosad (25 g/L suspension concentrate, Elector) were diluted in distilled water to the desired testing concentrations of either 0.04% (spinetoram only) or 0.08% (both) per label recommended premise spray use rate for controlling house flies with Elector. One square foot panels, obtained from commercial building suppliers, were composed of non-treated plywood, concrete and sheet metal. A second set of both plywood and concrete substrates were primed and painted using exterior grade latex white latex paint. Diluted materials were sprayed onto panels to the point of run-off (approximately 5 seconds per panel). A total of 4 panels were tested per treatment group (n=4). House flies were anesthetized using carbon dioxide and placed inside of plastic containers secured onto panels. There were 4 sub-replicates containers per panel, each container containing 10 mixed-sex adult flies (40 flies per panel). Glucose-saturated dental wicks were secured through a hole in each cup to provide a food and water source for flies. Panels remained upright throughout testing. Fly mortality and moribundity was assessed at post-exposure intervals of 4, 8, 24, 48 and 72 hours immediately following treatment applications and again on a weekly basis for 1 month.

Table 2 displays the geometric mean percent house fly reduction on treated panels.

TABLE 2

| Panel Composition | Test Material[1] | Application Rate (ppm) | % House Fly Mortality at 4 h | 8 h | 24 h | 48 h |
|---|---|---|---|---|---|---|
| Initial Activity | | | | | | |
| Unpainted Wood | Spinetoram | 400 ppm | 1.3 | 5.9 | 83.7 | 98.8 |
| | Spinetoram | 800 ppm | 0.6 | 39.4 | 100 | 100 |
| | Elector | 800 ppm | 1.3 | 74.9 | 100 | 100 |
| Sheet Metal | Spinetoram | 400 ppm | 19.7 | 91.8 | 100 | 100 |
| | Spinetoram | 800 ppm | 31.5 | 100 | 100 | 100 |
| | Elector | 800 ppm | 10.0 | 90.3 | 100 | 100 |
| Unpainted Concrete | Spinetoram | 400 ppm | 45.4 | 98.6 | 100 | 100 |
| | Spinetoram | 800 ppm | 42.5 | 99.2 | 100 | 100 |
| | Elector | 800 ppm | 11.3 | 93.5 | 100 | 100 |

TABLE 2-continued

| Panel Composition | Test Material[1] | Application Rate (ppm) | % House Fly Mortality at 4 h | 8 h | 24 h | 48 h |
|---|---|---|---|---|---|---|
| 4 Week Residual Activity | | | | | | |
| Unpainted | Spinetoram | 400 ppm | 0.6 | 0.6 | 4.7 | 12.1 |
| Wood | Spinetoram | 800 ppm | 0 | 0 | 22.6 | 61.2 |
| | Elector | 800 ppm | 0.6 | 0.6 | 97.8 | 100 |
| Sheet Metal | Spinetoram | 400 ppm | 0 | 40.6 | 91.3 | 97.3 |
| | Spinetoram | 800 ppm | 0.6 | 26.3 | 80.6 | 96.3 |
| | Elector | 800 ppm | 3.8 | 46.3 | 90.6 | 98.6 |
| Unpainted | Spinetoram | 400 ppm | 4.2 | 80.0 | 100 | 100 |
| Concrete | Spinetoram | 800 ppm | 31.3 | 98.8 | 100 | 100 |
| | Elector | 800 ppm | 13.1 | 93.1 | 100 | 100 |

Spinetoram was equivalent or superior to Elector, at one half the application rate on sheet metal and unpainted concrete panels. Spinetoram exhibited equivalent initial activity and marginally inferior residual activity when compared to Elector on unpainted plywood.

Surrogate Animal bioassay/ticks (*Amblyomma americanum*) and fleas: Topical exposure—Test materials are formulated in ethanol or acetone at the desired testing concentrations, typically 6% active ingredient or lower. Either doubling or log-dilutions are performed in ethanol to obtain additional testing concentrations (3.0, 0.3, 0.03, and 0.003 mg/cm$^3$). A tick containment unit is affixed to the back or adult male or female rats, and 0.05 ml of formulated test material is applied topically to the surface area inside of the containment unit. Materials are allowed to dry overnight, after which time 10 unfed dog tick nymphs are placed into each containment unit. A total of 5 rats are normally used for each test concentration. Ticks are allowed to attach and feed on treated animals for 48 h, after which time containment units are opened and live/dead ticks are enumerated. Rats may be co-infested with adult cat fleas at the time of tick infestation to obtain data for topical insecticide activity using the same animal. Spinetoram, in ethanol exhibited topical activity against tick nymphs equivalent to that of spinosad, while exhibiting approximately 5 to 10 times the potency compared to spinosad, in acetone.

Cattle Ectoparasiticide Test (CET)/Horn Fly (*Haematobia irritans*) and/or Adult Tick (*Amblyomma americanum*): Cattle are housed in environmentally controlled rooms, 1 or 2 animals per room that have screened doors and ventilation system to prevent fly escape. Following treatment application, a defined number of horn flies are released into each room (typically at or above economic threshold of 200 flies per animal). After defined periods of time, the numbers of live horn flies remaining on animals are enumerated. If a combination horn fly and tick experiment is conducted, adult lone star ticks are placed into surgical stockinette enclosures that are glued onto the backs of cattle. Cattle are restrained in a modified head gate within environmentally controlled rooms.

Horn flies may be enumerated, followed by determination of the numbers of dead ticks inside of containment units. Typically there are 2 containment units per animal and at least 2 animals per treatment group.

A) Single Dose Efficacy Testing and Comparison of Spinetoram with Elector against Lone Star Tick (*Amblyomma americanum*) Infestations on Cattle. Technical spinetoram was formulated as a 25 g/L suspension concentrate using the same formulatin components as found in Elector. Test material was applied to animals as a whole-body topical spray. Total of two animals per treatment group; each animal harbored ticks inside of 3 containment units (n=3 per animal or n=6 per treatment group). Concentrates (25 g/L) diluted in water; treatment level equivalent to marketed rate for Elector (0.5 g AI per animal). Table 3 displays the percent tick reduction (±SD) after indicated exposure interval on treated animals, and Table 4 displays speed of kill assessment for spinetoram and Elector against adult lone star ticks on cattle.

TABLE 3

| Treatment | Day 1 2 hr | Day 1 6 hr | Day 1 10 hr | Day 2 24 hr | Day 3 48 hr | Day 4 72 hr | Day 7 144 hr |
|---|---|---|---|---|---|---|---|
| Elector | 0 | 0 | 0 | 3.39 (±4.79) | 12.74 (±13.14) | 14.44 (±15.54) | 60.34 (±1.96) |
| Spinetoram | 0 | 0 | 0 | 0 | 8.14 (±6.17) | 8.14 (±6.17) | 46.67 (±18.87) |

TABLE 4

| Treatment | $ET_{50}$ (hr) | 95% CI (hr) | Slope | $R^2$ |
|---|---|---|---|---|
| Elector | 129.6 | 117.3-142.0 | 33.42 | 0.9145 |
| Spinetoram | 148.2 | 134.8-161.6 | 32.48 | 0.8776 |

Spinetoram exhibited equivalent activity (potency and speed of kill) to Elector against experimental lone star tick infestations, when applied topically to cattle at a dose of 0.5 g/animal.

B) Therapeutic and residual efficacy testing of spinetoram and Elector against horn flies when applied topically to cattle as a pour-on or topical spray. Spinetoram (120 g/L), Elector (25 g/L spinosad) as described previously were used. Test material was applied to animals as either a whole-body topical spray or neat pour-on. Spinetoram was diluted in water to 25 g/L prior to application as a pour-on. Both materials were diluted in water to 0.04% (400 ppm) for application as a whole-body spray in a total volume of 1 L per animal. There were a total of six animals per treatment group (n=6) plus six negative control animals. Beef and dairy cattle were used. Following treatments, horn flies were released into rooms harboring cattle. Live flies were enumerated 24 h following challenges. Table 5 displays geometric mean percent horn fly reduction following treatment of infested cattle with spinetoram pour-on (2 mg/kg) or spray (0.04% AI) and Elector pour-on (2 mg/kg) or spray (0.04% AI).

TABLE 5

| | GM percent horn fly reduction after 24 hrs | | | |
|---|---|---|---|---|
| | Spinosad | | Spinetoram | |
| Interval | Pour-on | Spray | Pour-on | Spray |
| Initial | 99.9 | 100 | 100 | 99.9 |

Spinetoram and Elector provided equivalent therapeutic efficacy when applied to horn fly infested cattle as either a pour-on (2 mg/kg) or whole-body topical spray (0.04% AI).

C) Efficacy Testing and comparison of topically applied spinetoram with spinosad for the treatment of *Boophilus annulatus* infestations on cattle. Technical spinetoram and technical spinosad both formulated as 25 g/L suspension concentrate formulations similar to commercial Elector. Stability assays (HPLC and LPT bioassays) were conducted to confirm potency over extended periods of time (5 weeks) at cool and shelf-temperatures. Cattle were pre-infested 21 d prior to treatment with larval-stage *B. annulatus* ticks resulting the presence of very high numbers of all three life-stages of this tick at the time of treatment. Test materials were diluted to 0.025% (250 ppm) and applied to cattle as whole-body topical sprays in a volume of 10 L per animal. There were a total of six animals per treatment group (n=6). Animals were housed in covered stalls under ambient conditions of temperature and humidity. Engorged, detached adult female ticks were retrieved from animals in each stall on a daily basis. Egg masses were weighed and eggs were set for hatching to assess viability. Efficacy was measured in terms of total numbers of female ticks per animal and index of fecundity (IF). Table 6 displays therapeutic efficacy of spinosad and spinetoram applied at 0.025% active ingredient (AI) as a whole-body spray to cattle infested with *Boophilus annulatus*, as reflected by the mean number of female ticks per calf, total index of fecundity (IF) and overall control of the IF (±SD). Table 7 displays the therapeutic efficacy (±SD) obtained against different parasitic life stages (adult, nymph, larva) of *B. annulatus* recovered from cattle treated with spinosad or spinetoram at 0.025% AI. Table 8 displays the residual efficacy or mean percentage control (±SD) of the IF obtained against *B. annulatus* ticks infested as larvae at weekly intervals after treatment.

TABLE 6

| Treatment | Number of ♀♀ Ticks per Calf | Total Index of Fecundity (IF) | Percentage Control of the IF |
|---|---|---|---|
| Untreated | 3506 ± 950 a | 399.5 ± 118.8 a | — |
| Spinosad | 2423 ± 311 a | 289 ± 40.1 a | 27.6 ± 10.0 a |
| Spinetoram | 2405 ± 306 a | 287 ± 35.4 a | 28.0 ± 8.9 a |

Means were tested by General Linear Model (GLM), 1-way ANOVA. Differences ($P < 0.05$) among means were separated using Tukey's all pairwise comparison. Means within the same column followed by different letters were significant at the $P < 0.05$ level.

TABLE 7

| | Percentage control for indicated group | |
|---|---|---|
| Parasitic Live Stage | Spinosad | Spinetoram |
| Adult | 18.5 ± 13.0 | 17.2 ± 25.0 |
| Nymph | 32.9 ± 10.8 | 31.6 ± 20.8 |
| Larval | 33.1 ± 16.6 | 38.6 ± 10.6 |
| P level within group | P > 0.2; NS | P > 0.3; NS |

Means were tested by General Linear Model (GLM), 2-way ANOVA with parasitic life stage and treatment group as main effects. NS denotes not significant.

TABLE 8

| Treatment Group | Week 1 | Week 2 | Week 3 | Week 4 |
|---|---|---|---|---|
| Spinosad | 97.6 ± 2.1 | 98.5 ± 1.2 | 89.4 ± 6.2 | 89.7 ± 4.8 |
| Spinetoram | 95.3 ± 3.3 | 96.7 ± 2.3 | 89.3 ± 8.0 | 80.4 ± 11.5 |

Spinetoram and spinosad exhibited poor initial/knockdown activity against *B. annulatus* but offered good protection from larval re-infestation of >96% through 2 weeks and >80% through 4 weeks (Table 8).

First evaluation of spinetoram as a topical spot-on for control of cat flea infestations. A study was conducted to evaluate the safety and efficacy of various doses of spinetoram applied topically for the control of fleas (*C. felis*) on cats. Twenty cats were allocated into four groups of five cats each.

The topical solutions were:

A) 202 mg/ml (theoretical) spinetoram in a vehicle of 50/50 w/w ethanol/isopropyl myristate)

B) 205 mg/ml (theoretical) spinetoram in a vehicle of 87/13 w/w benzyl alcohol/Dowanol DPM[di(propylene glycol)methyl ether]

C) 198 mg/ml (theoretical) spinetoram in a vehicle of 75/25 w/w isopropanol/Dowanol DPM[di(propylene glycol) methyl ether]

Vehicle controls were also employed. Solutions above targeted a point dose of approximately 27 mg/kg. Each animal in the three treatment groups received solution A, B, or C, applied as a topical spot-on to the skin between the shoulder blades on Day 0.

The animals were infested with fleas on Day −8, −1, 5, 12, 28, 35, and 42. Knockdown activity was evaluated 24 hours post-treatment, while residual efficacy was evaluated approximately 48 hours post reinfestation beginning with the Day 5 reinfestation.

All three formulations provided 100% therapeutic (initial) knockdown with 100% residual control through Day 14. Residual efficacy remained greater than 95% for at least a month, and greater than 93% for over a month, for all three formulations. Formulation B exhibited the longest period of residual activity with 99% efficacy through Day 37 and 90% efficacy through day 44. Formulations A and C fell below 90% efficacy sometime between Days 37 and 44. It is expected treatment levels of 40 to 50 mg/kg will provide 60 days or more of residual control against repeated flea infestations on cats.

Second evaluation of spinetoram as a topical spot-on for control of cat flea infestations. A study was conducted to evaluate the safety and efficacy of various doses of spinetoram applied topically for the control of fleas (*C. felis*) on cats. Twenty-eight cats were allocated into seven groups of four cats each.

The topical solutions were:

1) spinetoram 42% w/v (210 mg spinetoram/0.5 ml dose)
2) spinetoram 20.5% w/v (205 mg spinetoram/1.0 ml dose)
3) placebo/vehicle control Each formula was made based on the formulation B described above (87/13 benzyl alcohol/Dowanol DPM).

The groups were treated topically by spot-on application on Day 0, as follows:

| Group | Solution | Dose Rate | Dose Volume (mL/cat) |
|---|---|---|---|
| 1 | #3 | 1X | 0.52 |
| 2 | #2 | 1X | 1.04 |
| 3 | #1 | 0.8X | 0.42 |
| 4 | #1 | 1X | 0.52 |
| 5 | #1 | 1X | ~0.52 |
| 6 | #1 | 1.2X | 0.62 |
| 7 | #1 | 6X | 3.0 |

Group seven received a second application on Day 30. The solutions were applied at the stated dose volumes to deliver approximately 210 mg of spinetoram per cat at the 1× treatment rate, 168 mg per cat at the 0.8× treatment rate, and 252 mg per cat at the 1.2× treatment rate.

The animals were infested with fleas on Day −6, −1, 7, 14, 21, 28, 35, 42, 49, 56, and 63. Flea efficacy was evaluated approximately 24 hours post-treatment on Day 1, and approximately 24 hours post-infestation on Days 9, 16, 23, 30, 37, 44, 51, 58, and 65.

The spinetoram solutions achieved 100% control within 24 hours post-treatment. The 1× (210 mg) dose groups showed 100% control through Day 44 for solution #2, and through Day 65 for solution #1. All spinetoram treatments (0.8×-168 mg, 1×-210 mg, and 1.2×-252 mg) resulted in greater than 90% efficacy through 65 days post-treatment.

Third evaluation of spinetoram as a topical spot-on for control of cat flea infestations. A study was conducted to evaluate the speed-of-kill efficacy of spinetoram applied topically for the control of fleas (*C. felis*) on cats. Thirty-six cats were evenly allocated into six groups. One group was a no treatment and no vehicle group. On study days −8 and −1, each cat was infested with approximately 100 newly emerged, unfed adult fleas (*C. felis*), with an approximate split of 50/50 male to female flea. The topical solution used was spinetoram, on a pure basis, 39.6% w/w (210 mg spinetoram/0.5 ml dose), with benzyl alcohol and butylated hydroxytoluene. The treated groups were dosed once on Study Day 0 by application at the base of the skull at skin level, and flea counts were conducted as follows:

| Group | Post-treatment flea count |
|---|---|
| 1(untreated) | Study Day 0, and 24 hours after treatment |
| 2 | Study Day 0, and 1 hour after treatment |
| 3 | Study Day 0, and 24 hours after treatment |
| 4 | Study Day 0, and 4 hours after treatment |
| 5 | Study Day 0, and 8 hours after treatment |
| 6 | Study Day 0, and 12 hours after treatment |

By four hours after treatment, a 63.2% reduction in live flea numbers was observed. By eight hours post-dosing, the efficacy level had increased to 94.6%. Efficacy continued to improve at the twelve and twenty-four hour time points, with essentially complete control (98.6% and 100%, respectively).

At seven days after treatment, over 90% of fleas are killed within one hour of an additional infestation, with 100% reduction observed at hours 4, 8, 12, and 24 hours after the additional infestation.

At 28 days after treatment, a reduction of 80.7% of fleas was observed 1 hour after an additional infestation, 91.6% reduction at 4 hours, 98.5% reduction at 8 hours, and 100% reduction at both 12 and 24 hours.

As illustrated above, spinetoram displays both excellent residual efficacy and speed-of-kill efficacy.

We claim:

1. A method of controlling ectoparasite infestations of an animal which comprises topically administering a topical liquid pharmaceutical composition comprising an effective amount of spinetoram or a pharmaceutically acceptable salt thereof to said animal, wherein said animal is a companion animal, said ectoparasite is fleas, and said administration is carried out no more than every two weeks.

2. The method of claim 1 wherein said companion animal is a dog.

3. The method of claim 1 wherein said administration is spot-on, plunge or spray dipping, jetting with a hand held spray or in a race, or as a back-line spray or pour-on.

4. The method of claim 1 wherein said administration is carried out no more than monthly.

5. The method of claim 1 wherein said effective amount is 10 to 350 mg/kg of body weight of said animal.

6. The method of claim 1 wherein said flea is *Ctenocephalides felis.*

7. The method of claim 1 wherein said spinetoram or pharmaceutically acceptable salt is spinetoram.

8. The method of claim 1 wherein said companion animal is a cat.

9. A method for controlling flea infestations of an animal being a dog or cat which comprises topically administering a topical liquid pharmaceutical composition comprising an effective amount of spinetoram or a pharmaceutically acceptable salt thereof to said dog or cat, wherein said effective amount is 10 to 350 mg/kg of body weight of said dog or cat, and said administration is carried out no more than every two weeks.

10. The method of claim 9 wherein said flea is *Ctenocephalides felis.*

11. The method of claim 9 wherein said administration is carried out no more than monthly.

12. The method of claim 9 wherein said spinetoram or pharmaceutically acceptable salt is spinetoram.

13. The method of claim 9 wherein said animal is a dog.

14. The method of claim 9 wherein said animal is a cat.

* * * * *